(12) United States Patent
Ellison

(10) Patent No.: US 6,780,415 B2
(45) Date of Patent: Aug. 24, 2004

(54) ANIMAL MODEL FOR INFECTION BY AN APICOMPLEXAN PARASITE

(76) Inventor: Siobhan P. Ellison, P.O. Box 970, Fairfield, FL (US) 32634

( * ) Notice: Subject to any disclaimer, the term of this patent is extended or adjusted under 35 U.S.C. 154(b) by 72 days.

(21) Appl. No.: 10/152,960

(22) Filed: May 22, 2002

(65) Prior Publication Data

US 2003/0219381 A1 Nov. 27, 2003

Related U.S. Application Data

(60) Provisional application No. 60/302,007, filed on Jul. 2, 2001.

(51) Int. Cl.$^7$ ...................... A61K 39/00; A61K 39/002; A61K 39/005; A61K 39/015; C12N 15/00

(52) U.S. Cl. ................... 424/184.1; 424/265.1; 424/269.1; 424/272.1; 424/273.1; 435/440

(58) Field of Search .................... 424/184.1, 265.1, 424/269.1, 273.1, 272.1; 435/440

(56) References Cited

U.S. PATENT DOCUMENTS

2003/0171335 A1 * 9/2003 Stein et al. .................... 514/81

OTHER PUBLICATIONS

Dubey et al.; "Isolation in immunodefcient mice of Sarcocystis neurona from opossum (Didelpis virginiana) faeces, and its differentiation from Sarcocystis falcatula;" Internatioanl Journal for Parasitology 28; pp. 1823–1828; Sep. 22, 1998.

Dubey; "Migration and development of Sarcocystis neurona in tissues of interferon gamma knockout mice fed sporocysts from a naturally infected oppssum;" Veterinary Parasitology 96 (2001); pp. 341–351.

Speer et al.; "Ultrastructure of schizonts and merozoites of Sarcocysits neurona;" Veterinary Parasitology 95 (2001); pp. 263–271.

Lindsay et al.: "Determination of the activity of pyrantel tartrate against Sarcocystis neurona in gamma–interferon gene knockout mice;" Veterinary Parasitilogy 97 (2001); pp. 141–144.

Sommer et al.; "A comparison of sporozoite and cyst merozoite surface proteins of Sarcocystis;" Parasitology Research (1992); Feb. 15, 1992; pp. 398–403.

Blythe et al.; "Seroprevealence of antibodies to Sarcocystis neurona in horses residing in Oregon," Journal of the American Veterinary Medicine Association; vol. 210, No. 4, Feb. 15, 1997; pp. 525–527.

Bentz et al.; "Seroprevalence of antibodies to Sarcocystis neurona in horses residing in a county in southeastern Pennsylvania;" JAVMA vol. 210, No. 4, Feb. 15, 1997; pp. 517–518.

Saville et al.; "Seroprevalence of antibodies to Sarcocystis neurona in horses residing in Ohio;" Journal of the American Veterinary Medical Association; vol. 210, No. 4, Feb. 15, 1997; pp. 519–524.

Marsh et al.; "In Vitro Cultivation and Experimental Inoclation of Sarcocystis falcatula and Sarcocystis neurona Merozoites inol Guderigars (Melopsittacus undalatus);" The Journal of Parasitolgy; vol. 83, No. 6, Dec. 1997; pp. 1189–1192.

Mackay; "Serum antibodies to Sarcocystis neurona–half the horses in the United States have theml;" Journal of the American Veterinary Medical Association; vol. 210, No. 4, Feb. 15, 1997; pp. 482–483.

Dubey et al.; "Sarcocystis neurona N. SP. (Protozoa: AplcomplexA), The Etiologic Agent of Equine Protozoal Myeloencehalitis," The Journal of Parasitology, vol. 77, No. 2, Apr., 1991; pp. 212–218.

Fenger et al.; "Experimental induction of equine protozoal myeloencephalitis in horses using Sarcocystis sp. Sporocysts from the opossum (Didelphis virginiana);" Veterinary Parasitology 68 (1997); pp. 1999–213.

Ellison et al.; "In vitro culture and synchronous release of Sarcocystis neurona merozoltes from host cells;" Veterinary Parasitology 95 (2001); pp. 251–261.

Speer et al.; "An Ultrastructural Study of First–and Second– Generation Merogony in the Coccidian Sarcocystis tenella;" J. Protozool., Volum 28, No. 4, Nov. 1981; pp. 424–431.

Dubey; "A Review of Sarcocystis of Domestic Animals and Other Coccidia of Cats and Dogs;" Journal of the American Veterinary Medical Association, vol. 169, No. 10; Nov. 15, 1976, pp 1061–1078.

Ellison; "Molecular characterisation of a major 29 kDa surface antigen of Sarcocystis neurona;" International Journal for Parasitology 32 (2002); pp. 217–225.

O'Donoghue et al.; "The Asexual Pre–Csyt Development of Sarcocystid Tenella in Experimentally infected Sp cific Pathogen–Fre Lambs;" International Journal for Parasitilogy, vol. 14, No. 4, 1984; pp. 345–355.

Dubey et al.; "Equine Protozoal Myeloencephalitis In A Pony;" Journal of the American Veterinary Medical Association, vol. 188, No. 11, Jun. 1, 1996; pp. 1311–1318.

(List continued on next page.)

Primary Examiner—Mark Navarro
(74) Attorney, Agent, or Firm—Allen, Dyer, Doppelt, Milbrath & Gilchrist, P.A.

(57) ABSTRACT

An animal model for CNS infection by Apicomplexan parasites was produced by inoculating a homologous cell or other type of cell with the merozoite stage of the Apicomplexan parasite and inoculating the infected homologous cell or a cell line prepared therefrom back into the host from which it came. Such a model was used to develop drugs for treatment or prophylaxis, vaccines for protection from Apicomplexan diseases and diagnostic tests for determination active infection with Apicomplexan parasites.

12 Claims, 7 Drawing Sheets

OTHER PUBLICATIONS

Dubet et al.; "Development of Sarcocystis In A Mule Deer Transmitted Through Dogs and Coyotes;" Can. J. Zool. vol. 61, 1983; pp. 2904–2912.

Gray et al.; "Suspected protozoal myeloencephalitis in a two–month–old colt;" The Veterinary Record, Sep. 1, 2001; pp. 269–272.

O'Donoghue et al.; Characterization of Monoclonal Antibodies Against Ovine Sarcocystis spp. Antigens by Immunoblotting and Immuno–electron Microscopy; Veterinary Immunology and Immunopathology vol. 24, 1990, pp. 11–25.

Tenter et al.; "Differentiation of Sarcocystis Species In European Sheep By Isoelectric Focusing;" Parasitilogy Research, vol. 76, 1989; pp. 107–114.

Dubey et al.; *Sarcosystis neurona* Infections in Sea Otter (Enhydra Lutris): Evidence For Natural Infections With Sarcocystis And Transmission Of Infection To Oppossums (Didelphis Virginiana); The Journal of Parasitology, vol. 87, No. 6, Dec. 2001; pp. 1387–1393.

Dubey et al.; "The Gamma Interferon Knockout Mouse Model For *Sarcocystis neurona*: Comparison Of Infectivity Of Sporocysts And Merozoites And Routes Of Inoculation;" The Journal Of Parasitology, vol. 87, No. 5, Oct. 2001; pp. 1171–1173.

Granstorm et al.; "Equine Protozoal Myeloencephalitis;" Equinine Internal Medicine, S.M. Reed and W.M. Bailey, eds. W.B. Saunders Company, Philadelphia, Pa., pp. 486–491.

Cheadle et al.: "Neurologic Disease in Gamma–Interferon Gene Knockout Mice Caused By *Sarcocystis neurona* Sporocysts Collected From Opossums Fed Armadillo Muscle," Veterinary Parasitology, vol. 103 (2002); pp. 65–69.

Dubey et al.; "Characteristics Of A Recent Isolate Of *Sarcocystis neurona* (SN7) From A Horse And Loss Of Pathogenity of Isolates SN6 and SN7 by Passages in Cell Cultures;" Veterinary Parasitology, vol. 95, 2001; pp. 155–166.

Rosypal et al.; "Mice Lacking The Gene For Inducible Or Endothelial Nitric Oxide Are Resistant To Sporocyst Induced *Sarcocystis neurona* Infections," Veterinary Parasitology, vol. 103 (2002); pp. 315–321.

Cheadle et al., "Viability of *Sarcocystis neurona* sporaocysts and dose titration in gamma–interferon knockout mice," Veterinary Parasitology, 2001, vol. 95, pp. 223–231.

Lindsay et al., "Inoculation of *Sarcocystis neurona* merozoites into the central nervous system of horses," Veterinary Parasitology, 2000, vol. 92, pp. 157–163.

Fayer et al., "Sarcocystis Transmitted By Blood Transfusion," J. Parasitol, 1979, vol. 65 No. 6, pp. 890–893.

Johnson et al., "Experimentally Induced Sarcocystis Infection in Calves: Pathology," Am J Vet Res, Jul. 1975, vol. 36, pp. 995–999.

National Animal Health Monitoring System, "EPM—Equine Protozoal Myeloencephalitis in the U.S.," May 2001, National Animal Health Monitoring System, Fort Collins, CO #N312.0501.

* cited by examiner

Figure 1  Infection of S2O Hybridoma cells by *Sarcocystis neurona*
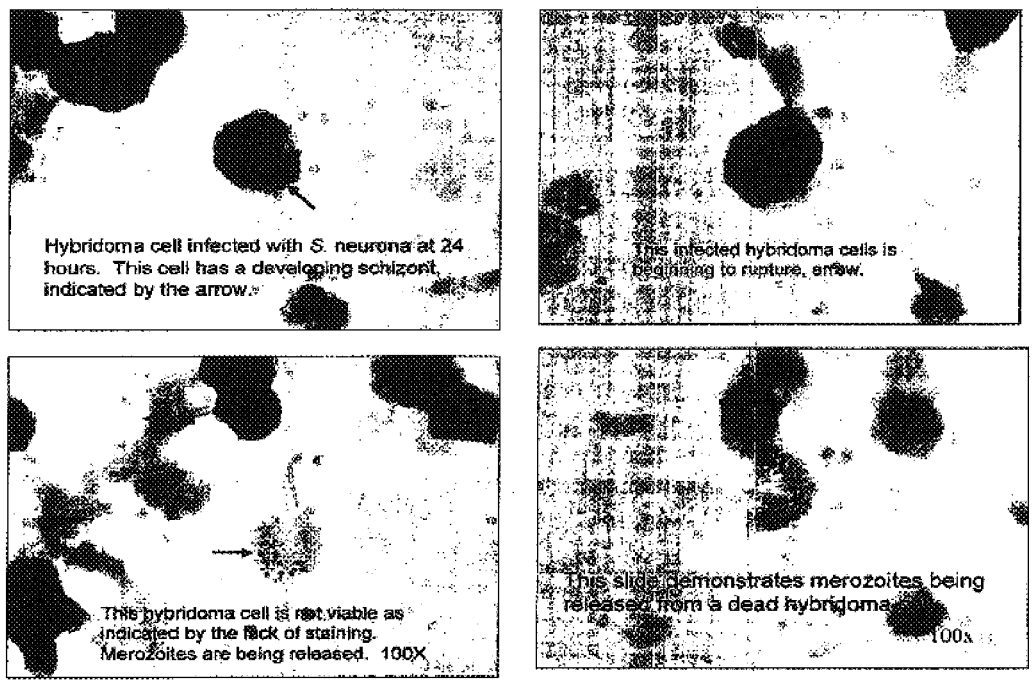

Figure 2  *S. neurona* merozoite has infected a B lymphocyte. The merozoite is indicated by the arrow.
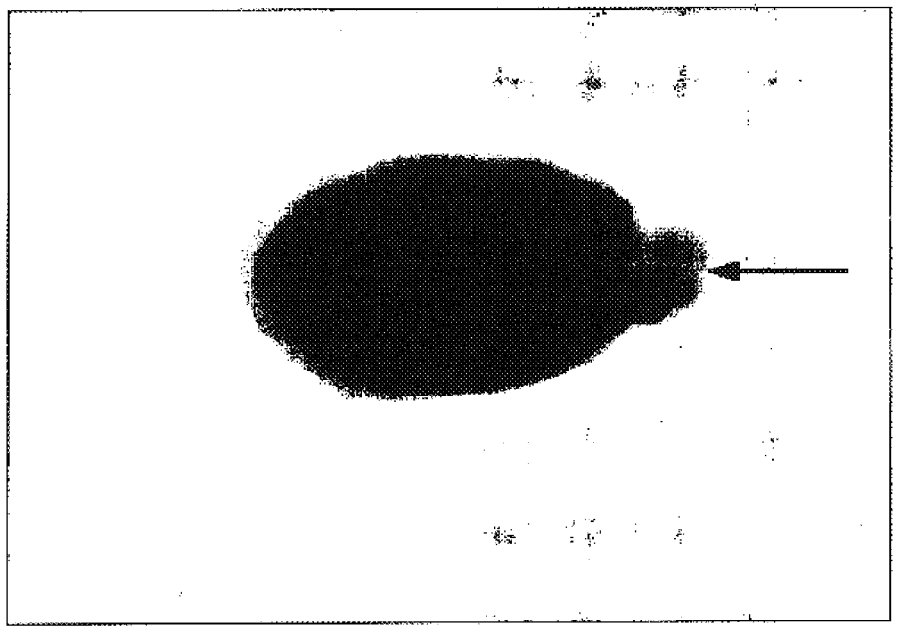

Figure 3. H&E stained *S. neurona* isolated from the spinal cord of the Pilot horse at 33 DPI, shown at 30 days after culture.

Figure 4. Merozoites isolated from the spinal tissues of a horse (high dose) experimentally infected with S. neurona. The slide was fixed with formalin and stained with Geimsa, 21 days in culture.

Figure 5. Three merozoites, arrows, in BT cell isolated from a horse (mid-dose), 21 days in culture, formalin fixed and stained with Geimsa, 100x Host cell nucleus

Figure 6. Merozoites, arrows, from 21 day culture of tissues from horse (low-dose) in BT cells. Merozoites were purified from tissue homogenate using immunoaffinity beads. Fixed with formalin and stained with Geimsa. 100x

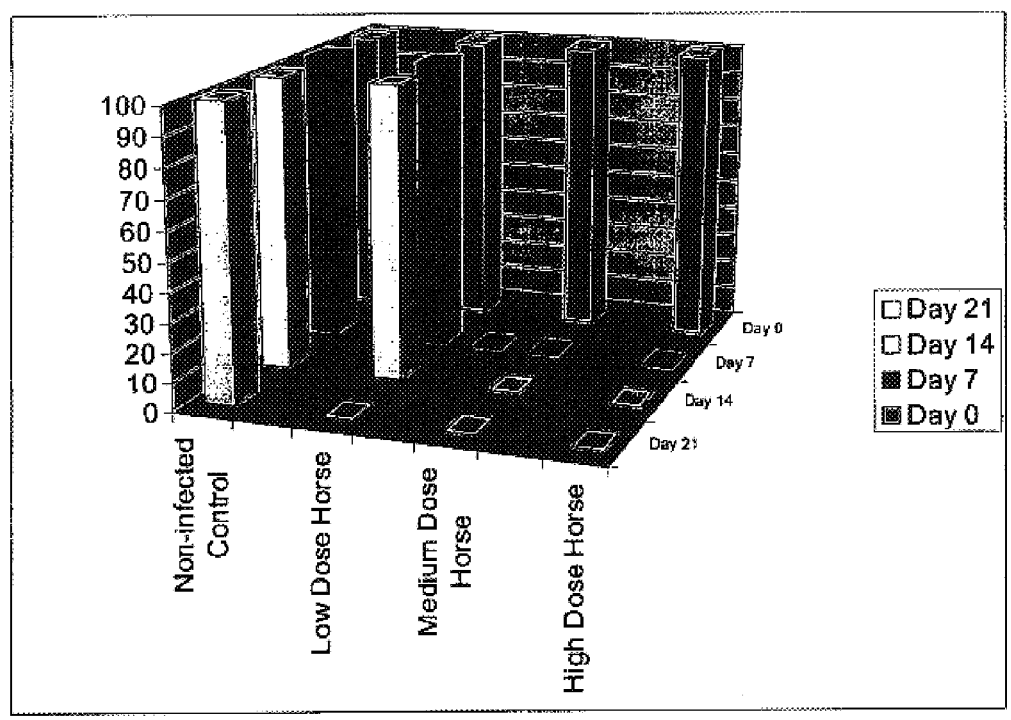
Figure 7   Demonstration of the Gamma Interferon Assay to Confirm Clinical EPM in the Horse

ANIMAL MODEL FOR INFECTION BY AN APICOMPLEXAN PARASITE

RELATED APPLICATION

This application claims priority from co-pending provisional application Ser. No. 60/302,007, which was filed on Jul. 2, 2001, and which is incorporated herein by reference in its entirety.

FIELD OF THE INVENTION

The present invention concerns an animal model for human and non-human diseases caused by Apicomplexan parasites including but not limited to *Sarcocystis neurona, Sarcocystis dasypus* (syn *S. neurona*), *Sarcocystis cruzi, Sarcocystis falcatula,* Sarcocystis sp., *Toxoplasma gondii, Neospora caninum, N. hughesi,* Eimeria and Plasmodium.

PRIOR ART

The following is a list of prior art references considered to be pertinent for the subsequent description:

1. Dubey J. P., Davis S. W., Speer C. A., Bowman D. D., de Lahunta A., Granstrom D. E., Topper M. J., Hamir A. N., Cummings J. F., and Suter M. M. 1991. *Sarcocystis Neurona* N. SP. (Protozoa: Apicomplexa), The etiologic Agent of Equine Protozoal myeloencephalitis. *J. Parasitol.,* 77(2): 212–218.
2. Blythe, L. L., Granstrom, D. E., Hansen, D. E., Walker, L. L., Bartlett, J., and Stamper, S. 1997. Seroprevalence of antibodies to *Sarcocystis neurona* in horses residing in Oregon. *JAVMA,* 210(4): 525–528.
3. Bentz, B. G., Granstrom, D. E., Stamper, S. 1997. Seroprevalence of antibodies to *Sarcocystis neurona* in horses residing in a county of southeastern Pennsylvania. *JAVMA,* 210(4): 517–518.
4. Saville, W. J., Reed , S. M., Granstrom, D. E., Hinchcliff, K. W., Kohn, C. W., Wittum, T. E., and Stamper, S. 1997. Seroprevalence of antibodies to *Sarcocystis neurona* in horses residing in Ohio. *JAVMA,* 210(4): 519–523.
5. Gray L. C., Magdesian, K. G., Sturges, B. K., Madigan, J. E. 2001. Suspected protozoal myeloencephalitis in a two-month-old colt. Vet Rec. 2001 September 1; 149(9): 269–73.
6. MacKay, R. J. 1997. Serum antibodies to *Sarcocystis neurona*—half the horses in the United States have them! *JAVMA,* 210(4): 482–483.
7. Dubey, A. P. 1976. A review of Sarcocystis of Domestic Animals. *JAVMA,* 169 (10):1061–1078.
8. Dubey, J. P., 1986. Equine protozoal myeloencephalitis in a pony. *JAVMA,* 188:1311–1312.
9. Granstrom, D. E, Saville, W. J. 1998. Equine Protozoal Myeloencephalitis In: S. M. Reed and W. M. Bailey, eds. *Equine Internal Medicine.* Philadelphia, Pa.: WB Saunders Company, 486–491.
10. Fenger, C. K., Granstrom, D. E., Gajadhar, A. A., Williams, N. M., McCrillis, S. A., Stamper, S., Langemeier, J. L., Dubey, J. P. 1997. Experimental induction of equine protozoal myeloencephalitis in horses using Sarcocystis sp. sporocysts from the opossum (*Didelphis virginiana*). *Vet Parasitol.,* 68:199–213.
11. O'Donoghue, P., Lumb, R., Smith, P., Brooker, J., Mencke, N. 1990. Characterization of monoclonal antibodies against ovine Sarcocystis spp. antigens by immunoblotting and immuno-electron microscopy. *Vet. Immunol. Immunopathol.,* 24(1):11–25.
12. Marsh, A. E., Barr, B. C., Tell, L., Koski, M., Greiner, E., Dame, J. and Conrad, P. A. 1997. In vitro cultivation and experimental inoculation of *Sarcocystis falcatula* and *Sarcocystis neurona* merozoites into budgerigars (*Melopsittacus undulatus*). *J. Parasitol.,* 83(6): 1189–1192.
13. Dubey J R, Rosypal A C, Rosenthal B M, Thomas N J, Lindsay D S, Stanek J F, Reed S M Saville W J. 2001. *Sarcocystis neurona* infections in sea otter (*Enhydra lutris*): evidence for natural infections with sarcocysts and transmission of infection to opossums (*Didelphis virginiana*). J Parasitol December; 87(6):1387–93.
14. Rosypal A C, Lindsay D S, Duncan R, Ansar Ahmed S, Zajac A M, Dubey J P. 2002 Mice lacking the gene for inducible or endothelial nitric oxide are resistant to sporocyst induced *Sarcocystis neurona* infections. Vet Parasitol February 4;103(4):315–21.
15. Dubey J R, Rosypal A C, Rosenthal B M, Thomas N J, Lindsay D S, Stanek J F, Reed S M, Saville W J. 2001. *Sarcocystis neurona* infections in sea otter (*Enhydra lutris*): evidence for natural infections with sarcocysts and transmission of infection to opossums (*Didelphis virginiana*). J Parasitol December; 87(6):1387–93
16. Rosypal A C, Lindsay D S, Duncan R, Ansar Ahmed S, Zajac A M, Dubey J P. 2002 Mice lacking the gene for inducible or endothelial nitric oxide are resistant to sporocyst induced *Sarcocystis neurona* infections. Vet Parasitol February 4;103(4):315–21
17. Cheadle M A, Ginn P E, Lindsay D S, Greiner E C. 2002. Neurologic disease in gamma-interferon gene knockout mice caused by *Sarcocystis neurona* sporocysts collected from opossums fed armadillo muscle. Vet Parasitol January 3;103(1–2):65–9
18. Dubey J P, Lindsay D S, Kwok O C, Shen S K. 2001. The gamma interferon knockout mouse model for *sarcocystis neurona*: comparison of infectivity of sporocysts and merozoites and routes of inoculation. J Parasitol October; 87(5):1171–3
19. Lindsay D S, Dubey J P. 2001. Determination of the activity of pyrantel tartrate against *Sarcocystis neurona* in gamma-interferon gene knockout mice. Vet Parasitol May 22;97(2):141–4
20. Dubey J P. 2001. Migration and development of *Sarcocystis neurona* in tissues of interferon gamma knockout mice fed sporocysts from a naturally infected opossum. Vet Parasitol February 26;95(2–4):341–51
21. Speer C A, Dubey J P. 2001. Ultrastructure of schizonts and merozoites of *Sarcocystis neurona.* Vet Parasitol February 26;95(2–4):263–71
22. Cheadle M A, Tanhauser S M, Scase T J, Dame J B, Mackay R J, Ginn P E, Greiner E C. 2001. Viability of *Sarcocystis neurona* sporocysts and dose titration in gamma-interferon knockout mice. Vet Parasitol February 26;95(2–4):223–31
23. Dubey J P, Mattson D E, Speer C A, Hamir A N, Lindsay D S, Rosenthal B M, Kwok O C, Baker R J, Mulrooney D M, Tornquist S J, Gerros T C. 2001. Characteristics of a recent isolate of *Sarcocystis neurona* (SN7) from a horse and loss of pathogenicity of isolates SN6 and SN7 by passages in cell culture. Vet Parasitol February 26;95 (2–4):155–66
24. Tenter , A. M., Johnson, M. R., Zimmerman, G. L. 1989. Differentiation of Sarcocyst species in European sheep by isoelectric focusing. *Parasitol. Res*. 76(2):107–114.
25. Sommer, I., Horn, K., Heydorn, A. O., Mehlhorn, H., Ruger, W. 1992. Acomparison of sporozoite and cyst merozoite surface proteins of Sarcocystis. *Parasitol Res*., 78:398–403.
26. Dubey, J. P., Kistner, T. P., and Callis, G. 1983. Development of Sarcocystis in mule deer transmitted through dogs and coyotes. *Can. J. Zool*., 61:2904–2912.

27. O'Donoghue, P. J. and Ford, G. E. 1984. The asexual pre-cyst development of *Sarcocystis tenella* in experimentally infected specific-pathogen-free lambs. *Int. J. Parasitol.*, 14(4):345–355.
28. Speer, C. A. and Dubey, J. P. 1981. An ultrastructural study of first and second generation merogony in the coccidian *Sarcocystis tenella. J. Protozool.*, 28(4): 424–431.
29. Johnson, A. J., Hildebrandt, P. K., and Fayer, R. 1975. Experimentally induced Sarcocystis infection in calves. Pathology *Am. J. Vet. Res.*, 36(7):995–999.
30. Fayer, R. and Leek, R. G. 1979. Sarcocystis transmitted by blood transfusion. *J Parasitol.*, 65(6):890–893.
31. Ellison, S. P., Omara-Opyeme, A. L., Yowell, Yowell, C. A., Marsh, A. E., Dame, J. B. 2002. *Molecular characterization of a major 29 kDa surface antigen of Sarcocystis neurona*. Int. J. Parasit. 32: 217–225.
32. Dubey, J. P., and Lindsay D. S. 1998. Isolation in immunodeficient mice of *Sarcocystis neurona* from opossum (*Didelphis viriniana*) feces and its differentiation from *Sarcocystis falcatula*. International Journal for Parasitology. 28:1823–8.
33. NAHMS. 2001. Equine Protozoal Myeloencephalitis (EPM) in the U.S. USDA:APHIS:VS, CEAH, National Animal Health Monitoring System. Fort Collins, Colo. #N312.0501.
34. Lindsay D S, Dykstra C C, Williams A, Spencer J A, Lenz S D, Palma K, Dubey J P, Blagburn B L. 2000 Inoculation of *Sarcocystis neurona* merozoites into the central nervous system of horses. Vet Parasitol. September 20;92(2): 157–63.
35. Ellison, S. P., Greiner, E., Dame, J. B. 2000. In vitro culture and synchronous release of *Sarcocystis neurona* merozoites from host cells. Vet. Parasitol. 1982: 1–11.
36. Speer, C. A., Dubey, J. P. 2001. Ultrastructure of schizonts and merozoites of *Sarcocystis neurona*. Vet Parasitol. 95: 263–271.
37. Dubey, J. P., Mattson, D. E., Speer, C. A., Hamir, A. N., Lindsay, D. S., Rosenthal, B. M., Kwok, O. C., Baker, R. J., Mulrooney, D. M., Tornquist, S. J., Gerros, T. C. 2001. Characteristics of a recent isolate of *Sarcocystis neurona* (SN7) from a horse and loss of pathogenicity of isolates SN6 and SN7 by passages in cell culture. Vet Parasitol. February 26;95(2–4):155–66

The acknowledgement herein of any of the above references is to allow the reader to gain appreciation of the prior art. The acknowledgement should, however, not be construed as an indication that these references are in any way relevant to the issue of patentability of the invention as defined in the appended claims.

Acknowledgement of the above references will be made by indicating the number from the above list.

BACKGROUND OF THE INVENTION

The development of effective treatments, therapies or diagnostics for Apicomplexan parasite diseases has been hampered by lack of suitable models for reproduction of the disease. This is at least in part due to the fact the Apicomplexan parasites such as *Sarcocystis neurona* cause diseases in immunologically privileged compartments such as the brain, spinal cord or fetal tissues, where the mammalian body cannot easily stimulate an immune response to control parasite invasion of these compartments. Illustratively, Equine Protozoal Myeloencephalitis (EPM) which is the leading infectious neurologic or abortigenic equine disease in the Western Hemisphere is caused by the Apicomplexan parasite *Sarcocystis neurona* (*S. neurona*). While the symptoms and effects of EPM have been recognized since the 1970's, it was not until 1991 that the protozoan parasite that causes EPM was isolated and cultured from a horse and given the name *Sarcocystis neurona*[1]. *Sarcocystis neurona* (*S. neurona*), recently recognized as *S. dasypus* (syn. *S. neurona*) cycles naturally between opossums and armadillos/raccoons. Recent investigations indicate that the feces of the opossum (the definitive host) may be the source of the infection for horses. Thus, the horse is an aberrant host, becoming exposed when it consumes infectious material from opossum feces. An aberrant host is a dead-end host, as infectious forms of the parasite are not passed from horse to horse or from infected horse to a definitive or true intermediate host. Incidence of EPM is likely greatest in areas with high opossum populations. EPM appears to have a sporadic distribution, although outbreaks have been reported on farms in Kentucky, Ohio, Indiana, Michigan and Florida [2–4].

A horse of any age, breed, or sex may be affected by EPM. The disease has been reported in a horse as young as two months of age, as well as one in its thirties [5]. In fact, any horse demonstrating neurologic abnormalities may be infected with an EPM-producing organism. In the horse, the most prominent EPM-producing organism, *S. neurona*, does not produce clinical signs of disease as a result of cyst formation, but as the cysts (sporozoites) convert to merozoites which make their way to the brain and spinal cord, where they proliferate and cause clinical disease. Clinical signs of a horse with EPM do not develop until the organism has crossed the blood brain barrier and is within the central nervous system. These signs include weakness, muscle atrophy, spinal ataxia, or "wobbling" and/or head tilt with asymmetry of the face (e.g., eyelid, ear, or lip). A severely EPM-affected horse may go down and be unable to rise. Lameness not traceable to orthopedic disease or any combination of the above signs may occur in early or less severe infections. In most cases, an affected horse is bright and alert with a normal appetite, hematological and biochemical blood values are usually in the normal range.

Surveys (using a positive serum test to immunoblotted *S. neurona* antigens to indicate exposure to the parasite) which were conducted in central Kentucky, one county in Pennsylvania and the entire states of Ohio and Oregon, have revealed that approximately fifty percent (50%) of the horses in the surveyed areas have been exposed to *S. neurona*[2–4, 6]. However, a positive test result on the immunoblot test does not necessarily indicate the presence of an active form of the disease. The incidence of the active disease appears to be much lower than the seroprevalence since less than 1% of seropositive horses are clinically affected [6]. At any rate, epidemiology and economic significance of *S. neurona* infection is substantial. Of animals clinically affected, 30–40% reportedly fail to respond to current therapy, and some of these animals die [6]. Conventional therapy relies on relatively non-specific drug/medications and/or combinations, the efficacy of which cannot be optimized because of the lack of a model of the disease. As such better and more effective prophylactic, or therapeutic modalities are required but cannot be thoroughly tested without an animal model that can predictably reproduce disease.

Currently, the only methods useful for diagnosis of this disease require removing cerebraispinal fluid from the horse—a method that is highly invasive and carries some danger. Originally, the diagnosis was based on the presence of antibodies to *S. neurona* in serum, though it is now known that a positive serum test cannot be used to make a diagnosis.

Such positive serum test simply indicates exposure to the parasite, not necessarily presence of the disease. Cerebral spinal fluid (CSF) testing is now believed to be the most useful test to assist in the diagnosis of this disease in a live horse [10]. However, even this test is flawed as clinically normal and vaccinated horses still seem to contain antibodies in the CSF. An improved animal model will be useful to develop less invasive diagnostic assays for EPM as well as to elucidate the immune response to vaccination and determine if the vaccine is efficacious In the case of EPM, sporocyst challenged horses are reported to produce antibodies in the CSF and this was taken as evidence of the parasites entry into the CNS [11]. However, neither isolation of parasites nor the presence of parasites in the CNS or any other tissue from the challenged horses was demonstrated. Therefore, Koch's postulate was not demonstrated, the disease EPM was not produced and the hoped-for model was not acceptable for the purpose of making drugs, vaccines and diagnostics.

An animal model, which has been used to date to study *S. neurona* isolated from natural cases of EPM, includes infection of nude mice or interferon gamma knock-out mice with sporocysts or culture derived merozoites [12]. These experiments result in neurological signs and isolation of the organism from the CNS [13–25]. However, the relevancy of this model is doubtful since these mice are immunodeficient; thus any immuno-based selection forces acting in normal animals are absent.

From the foregoing, it would be realized that despite a great deal of past and on-going effort, there remains an unfulfilled need for an animal model for Apicomplexan parasitic diseases including EPM.

SUMMARY OF THE INVENTION

In accordance with the foregoing, the present invention encompasses an animal model comprising reproducing clinical signs of Apicomplexan parasite disease by providing an Apicomplexan parasite which is incorporated in a host cell, such as a host lymphocyte cell, in an amount that is effective to cross the brain or placental barrier of the host, when the host is inoculated with the parasite-incorporated cell. The present invention is directed to a unique discovery that mammalian cells, specifically lymphocytes of all types and any other cell that can be activated so as to cross the blood brain barrier or the placental barrier, can be infected by merozoites of Apicomplexan organisms. After merozite infection of the mammalian cells, the infected cells can be used to infect mammals, reproduce clinical signs of Apicomplexan diseases and serve as models that are required for development of efficacious drug treatments, prophylactic modalities such as drugs and vaccines, and diagnostic tests for determination of Apicomplexan infections. Apicomplexan diseases described by the present invention include but are not limited to Sarcocystis, Toxoplasma and Neospora.

More specifically, the present invention is directed to an animal model for *S. neurona* that produces infection in the CNS of horses and reproduces the clinical signs of EPM. Without being bound to any particular theory of the invention, this model is based on the discovery that virulent merozoite cells of *S. neurona* can be induced to enter certain mammalian cells cultured in vitro and, as long as they retain their unextruded conoid, they can be transferred back to the homologous host. After transfer, the homologous host cells infected with virulent merozoite cells migrate via the blood to the central nervous system and can cross the blood brain barrier. The clinical signs of disease observed are produced by the virulent merozoites. In addition to the clinical signs, an animal model must produce serum and CSF antibodies against the EPM-producing organism, provide for isolation of the organism from the spinal tissues and/or CSF fluid in in vitro culture, and demonstration of the organism in the tissues of the horse.

Additionally, the present invention is directed to an animal model for *S. neurona* that produces infection in the fetus of pregnant mammals, potentially causing death of the fetus and/or abortion. This model is based on the discovery that virulent merozoite cells of *S. neurona* can be induced to enter certain mammalian cells cultured in vitro and, as long as they retain their unextruded conoid, they can be transferred back to the homologous pregnant host. After transfer to the homologous host, the homologous host cells infected with virulent merozoite cells migrate via the blood to the placenta and can cross the placental barrier. The clinical signs of disease observed are produced by the virulent merozoites infecting the fetus. For this model it is preferable to infect the filly or mare during the first trimester of gestation.

It is a distinct feature of the present invention that specific mammalian cells are infected in vitro with an EPM-producing parasite, allowed to reach the stage of growth in which the merozoite stage of the parasite is optimally virulent, and is used to cross the blood brain barrier. It is also a distinct feature of the invention that it has now been recognized that the Apicomplexan parasites can evade the immune response and to produce clinical signs of disease.

The present invention provides animal models for Apicomplexan infections including but not limited to Toxoplasma, Neospora, and/or Sarcocystis.

The present invention provides the models for development of preventive and/or therapeutic agents (drugs and vaccines) by demonstrating their effectiveness against Apicomplexan infections such as Toxoplasma, Neospora, and/or Sarcocystis.

The present invention also provides a method for developing diagnostic tests and determining their effectiveness in Apicomplexan infections such as Toxoplasma, Neospora, and/or Sarcocystis.

The present invention provides the animal model for the development of a new diagnostic test to diagnose EPM in the horse by measuring the γ-interferon response of horses to an antigen from an EPM-producing organism.

The present invention provides the animal model for the development of a new diagnostic test to diagnose EPM in the horse by measuring the antibody response to SAG-1, the outer membrane protein of *S. neurona*, in the CSF and/or serum.

DEFINITIONS

1. "Isolation" as used herein means recovery and in vitro growth of an organism from a clinically-diseased animal.
2. "Blood brain barrier" as used herein means the anatomical barrier to all molecules composed of two membranes in series: the lumenal and the ablumenal membranes of the brain capillary endothelial cell, which are separated by approximately 300 nm of endothelial cytoplasm. The blood brain barrier also consists of transport systems on both lumenal and ablumenal membranes of the endothelial cell for solute transcytosis from blood to brain. The blood brain barrier also contains a number of specialized carrier transport systems within the blood brain barrier that mediate brain uptake of circulating nutrients, such as glucose, amino acids, choline, transport or diapedesis across the anatomical barrier is allowed.
3. "Placental barrier" as used herein means the anatomical barrier to all molecules and components of two membranes in series that protects the fetus from infection and/or toxic substances.
4. "Virulent merozoite cell" as used herein means a merozoite producing proteins for attachment and invasion of host cells so that the parasite can attach to and enter a host cell where it replicates and responds to cell signals (parasite and host) resulting in the release of prodgeny capable of infecting more host cells.
5. "Conoid form" as used herein means the physical state of the apicomplex of parasites consisting of the conoid, conoid proteins, and actin/myosin fibers that attach to a host cell and produce infection wherein the conoid is maintained in an unextruded state.
6. "Parasite activated lymphocytes" as used herein means host cell lymphocytes that are capable of recognizing parasites, parasite antigens, or parasite proteins that are secreted. and by recognition, are capable of attaching to, engulphing, or responding to these components to result in infection of the host lymphocyte or modulation of the host immune system. 6. Homologous host as used herein means each animal from which a newly isolated cell or cell line has been obtained.
7. "Optimally virulent" as used herein means that the Apicomplexan merozoite is maintained in the conoid form.
8. "Modulate the immune system" as used herein means to orchestrate the immune system and its cascade of cellular, intercellular and intracellular reactions in a manner that favors the replication of the parasite.

DESCRIPTION OF FIGURES

FIG. 1 is a photograph of S2O hybridoma cells that have been infected with *Sarcocystis neurona*.

FIG. 2 is a photograph of a B lymphocyte infected by a *Sarcocystis neurona* merozoite.

FIG. 3 is a photograph of an H&E stained *Sarcocystis neurona* isolated from the spinal cord of the Pilot horse at 33 days post infection. The culture had been incubated 30 days.

FIG. 4 is a photograph of merozoites isolated from the spinal tissues of the high dose horse experimentally infected with *S. neurona*. Isolation was conducted by in vitro culture in BT cells after 21 days.

FIG. 5 is a photograph of merozoites isolated from the the spinal tissues of the mid-dose Horse experimentally infected with *S. neurona*. Isolation was conducted by in vitro culture in BT Cells after 21 days.

FIG. 6 is a photograph of merozoites isolated from the spinal tissues of the low-dose horse experimentally infected with *S. neurona*. Isolation was conducted by in vitro culture in BT cells after 21 days.

FIG. 7 is a graph demonstrating the gamma interferon response in horses prior to and after production of clinical disease of EPM. Prior to infection, the horses demonstrated high levels of gamma interferon. After infection there was a dose response relationship associated with the time at which gamma interferon stimulation to rSAG-1 was shut down.

DETAILED DESCRIPTION OF THE INVENTION

As set forth above, the present invention is directed to a unique discovery that mammalian cells, typically white blood cells and other cell that can be activated so as to cross the blood brain barrier, can be infected by merozoites of Apicomplexan parasites. After merozite infection of the mammalian cells, the infected cells can be used to inoculate mammals, reproduce clinical signs of Apicomplexan diseases, and thus serve as models for development of efficacious drug treatments, prophylactic modalities such as drugs and vaccines, and diagnostic tests for determination of Apicomplexan infections. Apicomplexan diseases described by the present invention include but are not limited to those caused by Sarcocystis spp, Toxoplasma spp and Neospora spp. A major advantage of the model of the present invention is that it can be used to reproduce Apicomplexan diseases in immunocompetent mammals, which can either be an intermediate non-human mammalian host or a non-human aberrant intermediate host.

Apicomplexan diseases for which the models are useful include but are not limited to EPM caused by *S. neurona, S. dasypus, S. falcatula* or *N. hughesi* (hereinafter designated as EPM-producing parasites) or Neosporosis caused by *N. hughesi, N. caninum*, bovine, equine or canine isolates (hereinafter designated as Neospora-producing parasites), Toxoplasmosis caused by *T. gondii*, and Eimeria spp producing coccidiosis in poultry.

Mammals useful fo this model include but are not limited to equines, bovines, canines, felines, goats, sheep, mice, rats, guinea pigs, and rabbits. Other animal models useful in the invention include chickens and turkeys.

The animal model of the invention is useful for the development of agents or treatment modalities, (e.g., antiparasitic drugs, antibodies, monoclonal antibodies, combinations of drugs, or administration regimens), having efficacy in the therapy of protozoan parasitic infection (e.g., EPM in the horse). The development may comprise screening for said agents or treatment modalities. For such screening, rodents or intermediate host mammals appropriate for the parasite, are inoculated with parasite-infected homologous cells and, following a time interval sufficient to allow development of infection within the brain or fetus of the inoculated host, the host is then administered with the tested agent or treatment modality and the therapeutic effect of such agent or treatment can then be evaluated, for example by determining the animals' median survival time or by means of histopathology of the brain or fetus or improvement in clinical signs.

When an immunocompetent mammal is used as a host, it is usually preferred to use a lymphoma cell line or some type of white blood cell, including but not limited to a lymphocyte, leukocyte or macrophage cell from the same species, particularly such a cell or cell line that is histocompatible to the host. Where an immune deficient host is used, the mammalian cell or cell line may be syngeneic, allogeneic or xenogeneic. When an immunocompetent horse is used as a host, it is preferred to use a mammalian white blood cell such as a lymphocyte cell or cell line from the same animal or such a cell line that is histocompatible to the host.

In accordance with the invention the *S. neurona* merozoite cell, a stage in parasite development shared by all other Apicomplexans including, but not limited to Toxoplasma and Neospora in addition to Sarcocystis spp, can be induced to enter mammalian cells, especially mammalian cells removed from host mammals, and cultured in vitro. The preferred cells for the present invention are white blood cells including but not limited to lymphocytes/leukocytes, B cells, resting B cells, T cells, monocytes, macrophages and lymphoma cells. Additional cells that can be used herein are cells or cell lines that are activated by antigens from the Apicomplexan parasite, cells that can be modified to cross the blood brain barrier, or cells and cell lines derived therefrom. These cells and cell lines can be cultured in vitro, infected in vitro and transferred back to the homologous host from which they originated. Upon transfer back to the homologous host, the parasite enters the blood stream and is carried to the brain or to the placenta (in pregnant hosts) where, when the cells containing still virulent merozoites are present, they cross the blood brain barrier and infect the spinal cord or the placental barrier and infect the fetus. Infection of the spinal cord results in clinical signs of disease whereas infection of the fetus can cause fetal death, weakness and/or abortion.

The animal model of Apicomplexan disease described herein generally comprises, but is not limited to the steps of: 1) infecting a susceptible homologous cell from a host animal with a merozoite stage of an Apicomplexan parasite; 2) inoculating said infected susceptible homologous cell into said host; 3) observing said infected host until clinical signs of the Apicomplexan disease develop, and 4) optionally, isolating the Apicomplexan from the infected host. Susceptible homologous cells are found by selecting a histocompatable cell from the mammal used for the model and demonstrating that the histocompatable cells are able to be infected in vitro with the Apicomplexan parasite. The in vitro infection of the susceptible homologous cells is accomplished by either exposing said cells growing in tissue culture to the Apicomplexan organism and observing the cells for growth of the merozoite stage, or simply exposing said cells to the Apicomplexan parasite in a stationary tube wherein the cells are incubated with the parasite until the parasite has entered the cells. The parenteral inoculation of the mammal can occur just once or can be repeated daily or weekly as often as necessary to produce clinical signs of disease.

The animal model can be more specifically described as comprising the steps of:
1) selecting a histocompatable cell from a mammal that is susceptible to infection with an Apicomplexan; 2) infecting said histocompatable mammalian cell in vitro with the Apicomplexan; 3) parenterally inoculating a mammal with said Apicomplexan-infected histocompatable mammalian cell; 4) observing clinical signs of the Apicomplexan disease; and optionally, isolating the Apicomplexan from the infected mammal.

Critical to the present invention is the maintenance of the merozoites in a virulent form. In accordance with the invention, the merozoites retain virulence as long as the conoid, found in all Apicomplexan organisms, is retained in the unextruded form. When Apicomplexan parasites enter cells, they extrude their conoid, thus producing infection of the cell. Within the infected cells, developing merozoites with intact conoids are again produced. If the merozoites are held too long in vitro, these merozoites will extrude their conoids and as such, cannot reinfect cells or cross the blood brain barrier.

Further in accordance with the invention the Apicomplexan merozoites maintain or are maintained in their conoid form as long as the cultured cells remain viable. When the cultured mammalian cell dies and lyses, the parasite is released. If the parasite does not contact another live acceptable mammalian cell within 5 hours, preferably within 30 minutes they will extrude their conoid and be ineffective for further infection. Therefore, it is optimum to culture the merozoites for transfer to the homologous host from between 1 minute and 48 hours, preferably from 4 hours to 24 hours prior to transfer back into the homologous host. One method used to optimize infection of the merozoite into the cell is to centrifuge the merozoite with the cell to be infected, preferably using density gradient agents to exclude extraneous cell types. A typical density gradient agent is Lymphoprep which can be obtained from Sigma Chemical Co.

It has also been realized that Apicomplexan parasites optimally enter white blood cells (lymphocytes, leukocytes and macrophages) of the host and by doing this evade the host's immune system. Lymphocytes are recognized as self. Specific cells useful in the present invention include but are not limited to B cells, T cells, resting B cells, antigen activated B and T cells, monocytes, macrophages and even lymphoma cells. The present invention utilizes this discovery by removing white blood cells from homologous hosts, infecting said white blood cells in vitro with virulent merozoites of the Apicomplexan and then transferring the infected lymphocytes back into the homologous host. Such transfer can be accomplished by administering the infected lymphocytes parenterally by any route including, but not limited to intravenous, intramuscular, subcutaneous, intratracheal, intraperitoneal, intranasal, intrathecal, or any combination thereof. The infected lymphocytes transfer to the blood stream where they are carried to the brain. These activated lymphocytes cross the blood brain barrier, infect the spinal cord and produce lesions. It is the production of the lesions that interfere with nerve transmissions that result in development of the clinical signs of disease.

The host cells and cell lines may be of any animal origin, e.g., human, equine, bovine, canine, feline, porcine, caprine, ovine, or murine.

Rodents inoculated with merozoite infected mammalian cells are useful, in accordance with the invention, as a non-host animal model for vertical transmission to a fetus or developing embryo. Horses inoculated with merozoite infected mammalian cells are useful, in accordance with the invention, as an animal model for EPM in the horse. Bovines or canines inoculated with such infected mammalian cells are useful, in accordance with the invention, as an animal model of Neosporosis for vertical transmission to a fetus or developing embryo. Finally, felines inoculated with such mammalian cells are useful in accordance with the invention as an animal model for Toxoplasmosis. Such a model can be advantageously used, for example, for screening or determining efficacy of drugs for treatment or prophylaxis of diseases such as EPM, bovine or canine Neosporosis, Toxoplasmosis and those caused by other types of Apicomplexan parasites. Such a model can also be advantageous for the study of mammalian cells and their mechanisms that breach the blood brain barrier and/or the placental barrier. Finally, the animals inoculated with such parasite infected mammalian cells are useful to elucidate the pathophysiology of disease with organisms that can modulate the immune system in favor of the pathogen.

More specifically described is an animal model for EPM in the horse, said model demonstrating clinical signs, serum and CSF antibody production against *S. neurona*, isolation of the organism from the spinal tissues and/or CSF fluid in in vitro culture, and demonstration of the organism in tissues by immunohistochemistry (IHC). As part and parcel of the invention, there is presented herein the recognition of the mechanism of this model as the problem transcended. The present invention describes the types of white blood cells of the horse used to cross the blood brain barrier and the placental barrier and explains how such parasites can evade the immune response of the horse and other mammals susceptible to Apicomplexan diseases.

An equine model of EPM disease described herein includes, but is not limited to the steps of: 1) removing blood from an equine to be infected with an EPM-producing parasite; 2) isolating the white blood cells from said blood; 3) inoculating said isolated white blood cells in vitro with the EPM-producing parasites such that they become infected by the EPM-producing parasites; 4) parenterally inoculating the same equine with the infected white blood cells; 5) observing said equine for clinical signs of EPM; and 6) optionally isolating the EPM-producing parasite from the blood, CNS or fetus of said equine. EPM-producing parasites are defined as *S. neurona, S. dasypus, S. falcatula* or *N. hughesi*.

In testing a treatment regimen for EPM, the steps of a treatment model of EPM include, but are not limited to: 1) producing clinical signs of EPM disease in a mammal as described above; 2) observing clinical signs in said mammal; 3) treating said clinically infected mammal with the drug to be tested; 4) observing said mammal for improvement in clinical signs; and 5) optionally, taking samples from said mammal and demonstrating the disappearance of the EPM-producing parasite from said samples.

In testing of a prophylactic regimen, the steps of a prophylactic model of EPM include, but are not limited to: 1) administering a prophylactic to be tested for effectiveness against EPM to one of two groups of mammals; 2) infecting both groups of mammals using the model of EPM described above; 3) observing both groups of mammals for development of clinical signs of EPM; 4) optionally, taking samples from said mammals demonstrating the presence or absence of the EPM-producing parasite in said mammals.

In testing of diagnostic products, the steps of the equine model of EPM include, but are not limited to: 1) removing blood and/or CNS samples from the mammals to be infected, prior to their infection; 2) infecting said mammals with the model of EPM as described above so as to produce clinical signs of EPM; 3) observing the clinical signs of EPM in said mammals; 4) removing blood, tissue and/or CNS samples from the mammals observed with clinical signs of EPM; and 5) demonstrating that the diagnostic test being evaluated differentiates between the blood, tissue and/or CNS samples from the mammals prior to infection and at or after the time that clinical signs of EPM are observed. The first and second samples can be the same or different and can be selected from the group consisting of blood and cerebral spinal fluid.

Diagnostic products produced using the described model include but are not limited to test systems that comprise one or more antibodies, one or more antigens or one or more PCR probes as the basis for detecting antigens, antibodies or homologous DNA/RNA in the mammal. Test systems include but are not limited to ELISA, immunoblot, western blot, dot blot, agglutination, hemagglutination, latex agglutination, PCR detection, etc.

The equine model of EPM has provided for development of a diagnostic test to accurately predict the active disease (infection) in horses prior to development of clinical signs. This diagnostic was used to determine whether the presence or absence of Interferon gamma (IFN γ) specific for SnSAG1 as assayed by RT PCR indicated EPM. Horses infected with varying doses of virulent merozoites according to the equine model of EPM were tested prior to infection, after infection and after development of clinical signs of EPM using the IFN γ specific for rSnSAG1 (a recombinant of the major surface antigen of *S. neurona*) as assayed by RT PCR. White blood cells from each horse were tested once a week for IFN γ stimulation by rSnSAG1. Serum samples from each horse were also obtained each week and were evaluated for IgG to rSnMSA-1 by direct ELISA. Both assays indicated that in the horses receiving medium to high doses (1,000 to 100,000) of virulent merozoites, the IFN γ response specific for rSnSAG1 was predictive of active disease. The IFN γ response went from normal (100% response at day 0) to no response by day 7 post infection in the medium and high dose horses. The low dose horse receiving only 100 virulent merozoites required 14 days before the IFN γ response specific for rSnSAG1 fell to 0. This horse developed transient clinical signs of EPM that may not be recognized by a horse owner. In the high and medium dose horses clinical signs did not develop until day 14 post infection. This experiment demonstrated that a diagnostic measuring the IFN γ response specific for rSnSAG1 can predict active disease in the horse prior to development of clinical signs. This analysis only resulted from the ability to use the equine model of EPM disease in the horse to demonstrate the effectiveness of the test. The advantage of this diagnostic test is that it can be conducted on serum making it optimal and non-invasive.

When the model is conducted in a rodent, the rodent is typically a mouse or rat and the mammalian lymphoma cell line is typically a murine lymphoma cell line. The horse is typically an immunocompetent horse and the cell or cell line is, typically isolated from the same animal. Two examples of such cells that were used effectively for the development of an infection model in accordance with the invention, were the S2O murine myeloma cell line, and another cell or cell line, newly isolated from each animal in accordance with the present invention, designated herein as "host cells" or homologous cells.

The model can also be used for designing vaccines having efficacy in the prevention of cell infiltration into the CNS or into the fetus of a mammal. This invention has distinctly provided a vaccine that contains conoid proteins or one that targets parasite activated lymphocytes would be effective in protecting from Apicomplexan diseases. Since the conoid is not present as a free structure in tissue culture growth of the merozoite, it would not be expected to produce antibodies in the host animal. However, a vaccine comprising one or more conoid proteins would stimulate antibodies to the conoid, binding this necessary factor for virulence of the merozoite and inhibit infection of host cells in vivo. The conoid proteins can be obtained by growing the Apicomplexan parasites so that they are maintained in the conoid form, isolating extracted conoid proteins and combining them in a purified or unpurified form with an adjuvant to produce a vaccine. Alternatively, the conoid proteins can be produced by art known recombinant techniques and combined with an adjuvant to produce a vaccine.

Preparation of vaccines that target parasite activated lymphocytes requires that the antigen or parasite protein that serves as a receptor is combinable with a receptor found on host T cells (TCR) by co-joining or otherwise adding together with the host TCR. When presented together on the lymphocyte there results a stimulation of automatic cell death of the T cell further resulting in destruction of the clone or T cell population that can be invaded by and carry the parasite across the blood brain barrier or the placental barrier. Therefore, a vaccine for protecting against Apicomplexan parasite diseases would comprise a component that targets activated lymphocytes to produce cell death of the T-lymphocyte carrying the Apicomplexan parasite. More specifically, this vaccine would comprise T cells that are natural killer cells or cytotoxic T lymphocytes having a T cell receptor with an alpha, beta or zeta chain joined to a target antigen of the T cell population to be eliminated. Therefore, recognition of the antigen target would activate the killer cell thereby inhibiting or destroying the T cell. Additionally, cells that are normally inefficient antigen presenting cells, such as resting B cells, can be upregulated by chimeric molecules made up for example of a zeta fusion with SAG1 of *S. neurona* thereby mediating the efficient activation of T helper cells to act in a similar manner as described above. Such a vaccine would preferably comprise an adjuvant.

Adjuvants useful in vaccines include but are not limited to polymers such as HAVLOGEN®, POLYGEN, Carbopol® based, acrylic acid based, acrylates, oil in water such as EMULSIGEN®, water in oil, water in oil in water, aluminum hydroxide, aluminum sulfate, liposome based, any any other type that successfully stimulates a B cell or T cell immune response.

Once prepared, these vaccines are tested for efficacy in mammals such as rodents, horses, bovines, canines, felines, swine or poultry that first receive the vaccine being tested and then are inoculated with parasite-infected mammalian cells, as above. The effect of the vaccine in preventing infiltration of the parasite-infected cells into the CNS, fetus or other tissues can then be determined, e.g. by histopathology, cultivation and other such methods known in the art.

A unique finding in accordance with the invention is that the murine model is most effective for evaluating effectiveness of inhibition of vertical transmission to the fetus using newly bred rodents, i.e., infection at breeding. Accordingly, use of newly bred rodents as the inoculated host is preferred in accordance with the invention. The murine host may be an immunocompetent host that may be selected from a range of rodents customarily used in laboratories, e.g., BALB/c mice or CF-1. Alternatively, the rodent host may be an immunodeficient host, e.g., a genetically immunodeficient rodent such as the SCID, Nude, Beige and BNX mice, or a rodent which was immunocompromised by irradiation or appropriate chemical treatment and whose immune system was then reconstituted by a bone marrow of SCID mice.

A murine model of EPM disease described herein includes, but is not limited to the steps of: 1) infecting lymphoma cells, such as the S2O cell line, in vitro with *S. neurona*; 2) parenterally inoculating the *S. neurona* infected lymphoma cells into rodents; 3) observing said rodent for clinical signs of EPM; and 4) optionally, isolating *S. neurona* from the blood, CNS or fetus (if the rodent is pregnant) of said rodent.

The present invention also provides, by one of its aspects, a non-human animal model for producing monoclonal antibodies, comprising a rodent host being inoculated systemically with mammalian cells infected with an Apicomplexan parasite, which is either a mammalian lymphocyte cell line or a mammalian cell line derived from a lymphoma cell line capable of stimulating an immune response in the inoculated host and not against host cells making the production of monoclonal antibodies and screening of these hybridomas simpler.

Dubey and workers have reported that *S. neurona* will lose virulence for interferon gamma knockout mice when maintained in continuous culture. The continuous culture described by Dubey et al. was of mammalian origin. The *S. neurona* strain (Pathogenes Isolate 3) used in the studies of this invention has been maintained in a virulent state in mammalian culture. The inventors have determined that the successful infection of equine white blood cells, including lymphocytes, and thus the successful production of EPM in this model is more closely related to maintaining the conoid of the Apicomplexan, *S. neurona*, in the unextruded state at the time of infection than on limiting the number of passages in in vitro mammalian cell culture. The present invention provides for the successful infection of horses with *S. neurona* and recovery of the organism from the CSF, said successful infection being due to infecting the correct mammalian (equine) cell with the parasite with the most virulent form (conoid un-extruded) of the parasite. Once infected, these cells can be transported across the blood brain barrier. It is most interesting that the infection model described herein reproduces Apicomlexan disease irrespective of the antibody status of the animal.

The invention will now be illustrated by some non-limiting, specific embodiments described in the following examples.

EXAMPLE 1

Generation of *Sarcocystis neurona* Infected S2O Cells

Murine S2O cells (ATTC CRL 1581) were propagated in 8 ml Dulbecco's Modified Eagle's Medium (DMEM, Gibco) or RPMI (Gibco) supplemented with 10% heat inactivated horse serum (Gibco), Penicillin (50 u/mil) and Streptomycin (50 mg/ml) in 25 cm flasks. The S2O cells were maintained at 37° C. in a humidified atmosphere containing 5% $CO_2$. The S2O cells were grown in continuous suspension culture by dilution of the stock culture 1:3 (16 ml) with fresh culture medium, supplemented as above, twice a week. To infect the S2O cells with *S. neurona* merozoites, a seed volume of the cultured cells containing ten thousand S2O cells, was added to an inoculum of 1000 culture derived merozoites in a 50 ml conical tube and centrifuged 20 minutes at 600×g. The cell pellet was resuspended in a 25 $cm^2$ flask containing 8 ml fresh culture media as described above and incubated at 37° C. After 24 hours incubation the infected S2O cells were selected in vitro using a density gradient (Lymphoprep) by known methods. Briefly, the culture medium was removed by centrifugation at 800×g and the cell pellet resuspended in heat inactivated serum diluted 50% with culture medium. Six ml of diluted infected cells were layered over a cushion of 3 ml Lymphoprep and then centrifuged for 20 minutes at 800×g. The pelleted cells were retained (infected) and the band of cells at the interface (uninfected) was discarded. To maintain a flask of infected cells without isolation, 10,000 fresh S2O cells were added once weekly to the flask in 0.25 volume of media (2.5 ml). The cell culture was evaluated once a week by staining a 100 microliter aliquot of methanol fixed culture with Geimsa and evaluating the merozoites by microscopy at 100×. FIG. 1 is a photograph of S2O cells infected with *S. neurona* merozoites. Not only were these cells infected with *S. neurona* merozoites, they also produced antibodies to the surface antigen (SAG1), said antibodies being recoverable in the culture supernatant.

The infection of S2O cells demonstrates that lymphoma cells can be infected by merozoites of *Sarcocystis neurona*. The fact that these infected S2O cells produced antibodies to the *S. neurona* merozoites, and that the antibodies were released into the culture media, indicated that this ability to infect S2O cells by Apicomplexan merozoites also provides for a new method for production of monoclonal antibodies. Not only do the infected cells produce antibodies, but such infected cells can also be used to inoculate mice from which spleens may be harvested. When infected in this way the mouse only produces B cells to the parasite and not to the S2O cells which are considered autologous. The harvesting and production of B cells to produce monoclonal antibodies are well known to those that practice the art.

To infect mice or other cells the continuous cell cultures of merozoite infected S2O cells were maintained for 15 days and then harvested by centrifugation using Lymphoprep to isolate uninfected cells. The pelleted infected cells (in the conoid form) were diluted as needed for infection. The $TCID_{50}$ for the infected cell inoculum was evaluated by placing aliquots of infected cells, serially diluted, on BT (Bovine Turbinate, ATTC) cells grown in a monolayer in a 96 well tissue culture plate, incubating for 7 days, and staining the monolayers. The preparation was considered infectious if a $TCID_{50}=300$ was the last dilution showing 50% of the monolayers (n=6) if 1600 host cells were used.

EXAMPLE 2

Generation of Infected Equine Cells

*S. neurona* was maintained as previously described in EXAMPLE 1. Parasites were freshly harvested and used to infect homologous cells obtained from the hosts (horse) peripheral blood. The host cells were concentrated to obtain an enriched fraction of white blood cells (lymphocytes). Culture derived merozoites grown and maintained in bovine turbinate (BT) cells as previously described were removed from a flask that contained free merozoites in the media and centrifuged at 600×G for 10 minutes at room temperature. The merozoites were resuspended in RPMI growth media and counted using a hemocytometer. Twenty four thousand equine purified lymphocytes obtained from the peripheral blood were added to each of six microfuge tubes and twenty four thousand merozoites were added to each tube. The tubes were incubated for 2 to 24 hours 37° C. in 5% $CO_2$. The tubes were under layered with density 1.077 Optiprep and 250 $\mu$l of phosphate buffered saline (PBS) was over layered on the gradient. The microfuge tube containing the gradient was centrifuged at 200×G for twenty minutes at room temperature. The supernate above the interface was collected and diluted with an equal volume of RPMI medium and centrifuged at 5000×G for five minutes. The number of viable parasites in homologous lymphocytes was determined by counting 5 $\mu$l of infected cells dried on a slide and stained with Geimsa. It was determined that the parasites had entered cells at 5 hours and the infected cells were added back to a 6 ml EDTA tube containing fresh peripheral blood from the homologous horse. An example of such an infected B lymphocyte of a horse is shown in the photograph in FIG. 2.

All parasite preparations used for challenge were tested for the ability to infect in vitro cells by inoculation of a duplicate sample on to bovine turbinate cells. Aliquots from all parasite preparations used for animal infections were observed to enter host cells and complete one asexual cycle within three days. Parasite preparations were tested for the ability to infect equine cells obtained from peripheral blood on days 1–15 and maintain their infectivity for bovine turbinate cells using an in vitro viability assay. A 5 $\mu$l sample of the infected equine purified lymphocytes was used to form thin smears that were stained with Geimsa and examined by light microscopy. Initially it was determined that lymphocytes were primarily infected with merozoites after 2 to 5 hours incubation although monocytes contained some parasites. A few monocyte cells contained more than one merozoite. The merozoites had entered cells by 5 hours although, at high ratios of parasite to host cells, a few parasites remained free in the media. When freshly infected lymphocytes were added to adherent BT cells in vitro, developing schizonts were visible in 24 hours. When infected equine lymphocytes were incubated in RPMI for 24 or 48 hours and then transferred to monolayers of BT cells the merozoites remained viable however at 48 hours lymphocytes were ruptured by the developing schizont.

This experiment demonstrated that *S. neurona* merozoites can be cultivated in vitro in equine cells and that the merozoites enter the equine cells within 5 hours of exposure to the cells.

EXAMPLE 3

Development of an Evaluation System for an Equine Model of EPM

A lameness evaluation system was developed according to information known in the art relative to EPM.

Animals were examined for lameness daily. Stride length was measured once a week. Neurological status was evaluated once a week and documented by video camera and recorded on an "EPM clinical neurological examination" form. The lameness was scored as according to the following definitions:

Grade 0—not lame.

Grade 1—Lameness was not observed at a walk but was recognizable at a trot. The horse's head would drop when weight was placed on the sound limb and rose to a more normal height when weight was placed on the affected side. For hind limb lameness, a mild symmetry in the glufteal rise was noted. No changes in head and neck movement were evident.

Grade 2—The lameness was noticeable at a walk although no change in the movement of the head and neck were noticed at this gait. At a trot, the horse would lift both the head and neck when the affected limb was placed on the ground and the lameness became more obvious. For hind limb, a greater degree of asymmetry of glutteal rise and shortened duration was noted, a slight dropping of the head would be noted when the opposite forelimb hits the ground.

Grade 3—The lameness was obvious at both a walk and the trot with the head and neck lifting when the affected limb was weight bearing. For the hind limb, head nodding when the opposite forelimb hit the ground while trotting was obvious.

Grade 4—Non-weight bearing on the affected limb.

Ataxia were be scored as:

Grade 0—No deficits indicated a normal animal.

Grade 1—Deficit just detected at normal gait.

Grade 2—Deficit easily detected and exaggerated by backing, turning, swaying, l loin pressure or neck extension.

Grade 3—Deficit very prominent on walking, turning, loin pressure or neck extension.

Grade 4—Stumbling, tripping and falling down spontaneously.

Grade 5—Recumbent, unable to rise. The average of three stride lengths was used to determine the stride length. These measurements were collected at the walk. The animals gait was recorded by video tape at weekly intervals.

A Clinical Pathology Evaluation System was Developed

A complete blood count (CBC) was obtained once a week. White blood cells from each animal were tested once a week for IFN γ stimulation by recombinant protein representing the major surface antigen of *S. neurona* (rSnSAG1)—see EXAMPLE 6 below. Serum samples obtained each week were evaluated for IgG to rSnMSA-1 by direct ELISA. Reaction to native *S. neurona* antigen separated by SDS PAGE was determined by immunoblot. At 67–8 days the horses were humanely euthanized and CSF collected for antigen and antibody determination. Gross necropsy was performed and samples of liver, lung, spleen, brain, and cervical spinal cord were placed in zinc buffered formalin for histopathology and immunohistopathology using monoclonal antibody (mAb) to SnMSA-1. Additionally, sections of cervical spinal cord were examined for areas of discoloration and discolored areas were macerated and placed in tissue culture flasks containing BT cells to attempt isolation of *S. neurona* merozoites. The remaining sections of spinal cord were macerated and the suspension centrifuged at 200×G for 3 minutes. The supernate was incubated with immuno affinity beads coated with mAb to SnSAG1 for 2 hours at 37° C. The beads were collected, washed, and placed on a 1.077 density gradient and over layered with PBS as previously described. After centrifugation at 13,000 for 10 minutes the supernate was removed and placed on a 30% confluent monolayer of bovine turbinate cells.

EXAMPLE 4

Infection of a Horse to Demonstrate the Equine Model of EPM

A 6 mL sample of blood of a horse that was seronegative to EPM using the IFN γ method of diagnosis (described in EXAMPLE 6), was removed. The lymphocytes were separated out, cultivated in vitro as described in EXAMPLE 2 and infected with 100,000 merozoites of *S. neurona*. Five hours after infection, all of the merozoite-infected equine lymphocytes were inoculated back into the homologous horse (the Pilot horse). A similar infection procedure was repeated three more times on days 7, 14, and 21.

The pilot horse was observed daily for clinical signs of EPM. This horse was ataxic 10 days after the first treatment. He became noticeably lame in the rear with a spastic movement of the pelvic limb and was graded 2 for lameness and 3 for ataxia. The horse began to lose weight, drooled and dropped feed. The body condition of the horse improved with increased feed and alfalfa hay. The lameness seemed to plateau for seven days but became worse after the third treatment. His clinical signs progressed, he showed a disoriented demeanor and moderate, generalized weakness. He was euthanized 34 days after the first injection.

The spinal cord was removed and examined, gross visible lesions were divided for histopathology and some areas from the lesions were placed with host cells to recover organisms by culture. *Sarcocystis neurona* was visible by immunohistochemical analysis (IHC) and organisms were recovered from the spinal cord cultures (see FIG. 3). The cultures were determined to be growing *S. neurona* by five days in culture demonstrating the overwhelming infection of these tissues This study demonstrated that lymphocyte cells from experimental horses supported the invasion and replication of *S. neurona*. These homologous (autologous) infected cells were then injected back into the host. Infections with clinical signs of disease were observed in ten days when 100,000 merozoites were used to infect the Pilot horse. In an effort to make the ataxia more demonstrable three more challenge injections were given. When it was clear 33 days post infection that the horse had clinical EPM, the horse was euthanized and merozoites were recovered from spinal tissues by in vitro culture.

This is the first demonstration of the successful infection of a horse with *S. neurona* to produce the clinical signs of EPM and recover the causative agent from the spinal cord.

EXAMPLE 5

Dose Titration Study Using the Equine Model of EPM

The previous study determined the number of organisms necessary to induce clinical EPM disease in horses using *S. neurona*. It was the goal of this study to use the infection model to determine its feasibility in determining the effectiveness of drugs and/or vaccines to prevent or treat clinical EPM caused by *S. neurona* as well as to demonstrate the inhibition of proliferation of this parasite in the CNS in the challenged horse. In an effort to adapt the model to a reasonable scenario for the natural course of disease a daily challenge dose, administered each day for fifteen days was used in a dose titration experiment Four immunocompetent horses were used in this experiment. Three of the horses were selected for infection with varying amounts of homologous cells infected with *S. neurona* merozoites as described in EXAMPLE 4. The fourth horse received uninfected homologous cells and served as a non-infected control. The horses were observed according to the procedure described in EXAMPLE 3 and IFN γ was analyzed as described in EXAMPLE 6. The low dose horse received 100 merozoite-infected homologous cells, each day for 15 days post initiation of infection. The medium dose horse received 1000 merozoite-infected homologous cells each day for 15 days post initiation of infection. The high dose horse received 10,000 merozoite-infected homologous cells each day for 15 days post initiation of infection.

All horses used in the titration study remained healthy and increased in weight during the duration of the study. The hematocrit of two horses (medium and high dose challenge) decreased between day 0 and day 7 and then returned to normal for the remainder of the study. An increase in the protein in the CSF in the medium and high dose horses was noted at 7 days post challenge. The CSF fluid was cleared by centrifugation and the resulting pellet was cultured on a 60% confluent monolayer of BT cells. The cultures containing the pellets derived from the CSF pellet from medium and high dose horses contained *S. neurona* merozoites. *Sarcocystis neurona* schizonts from these cultures were observed ten days following introduction of the CSF pellet into the flask containing the BT monolayer. The CSF fluid from the non-infected control horse and the low dose horse did not contain significant protein and did not contain *S. neurona* when examined by Geimsa staining or culturing a sample of the 50 μl CSF fluid remaining after centrifugation.

The control horse (Horse 1) remained normal throughout the study. The low dose horse (Horse 2) experienced neck pain at day 13 with no signs of inflammation. She was reluctant to bend her neck and was unable to eat from the ground. When she was asked to turn or trot she experienced muscle fasciculation involving the muscles surrounding the left eye and left lateral neck. After four days the mare had returned to normal. This horse exhibited an abnormally wide gait more obvious at the trot on day 14. The gangly gait did not progress. The medium dose horse (Horse 3) began dragging a toe and showed a weakness in the pelvic limbs by day 14. This filly was dragging the right toe by 21 days and was stumbling when asked to trot. The filly progressed with mild rear limb weakness and began to show some thoracic limb weakness by the end of the trial. The high dose horse (Horse 4) was the oldest and remained normal until the last ten days of the trial. At this time she was slightly lame at a trot and unable to canter in a tight circle. All three horses showed one-sided mild facial paresis by week 4 of the study.

Horses 1, 2 and 4 were negative for antibodies to *S. neurona* antigens separated by SDS and detected by immunoblot when the serum was diluted 1:50 at the beginning of the trial. Horse number 3 was positive for antibodies detected by immunoblot at the start of the trial when the serum was diluted 1:50. By day 7 of the trial horses 2 and 4 had detectable IgG to *S. neurona* by immunoblot. Horses 2, 3, and 4 continued to have antibodies to *S. neurona* for the duration of the trial. Antibodies were detected to *S. neurona* in the CSF, diluted 1:10, and tested by immunoblot in horses 2, 3, and 4 by day 7 of the trial. The control horse (Horse 1) remained negative throughout the duration of the trial for antibodies to *S. neurona* in both the serum and CSF.

*Sarcocystis neurona* was isolated from the spinal cord of the three challenged horses. The cultures that included a purification step using immunoaffinity purified beads followed by sub-culture into 24 well plates were positive for the growth of *S. neurona* by 10 days for horse 3 and 4 and by day 21 in horse 2. FIGS. 4, 5 and 6 are photographs of the merozoites cultivated from the high dose, medium dose and low dose horse, respectively. No merozoites were recovered from the tissues of the control horse.

The results of the titration study showed that homologous (autologous) cells infected with 1000 or 10,000 organisms given daily for seven days induced significant changes in the CNS and allowed recovery of the organism in vitro. Clinical signs were observed fourteen days after the first day of challenge in one horse. The clinical signs remained slight in three horses during the duration of the study however the signs seemed dose related and slowly progressive. Where the Pilot horse receiving 100,000 merozoite-infected homologous cells (EXAMPLE 4) became very ill the horse that received 100 merozoites in this study was least affected. Due to the termination of this study by euthanasia so as to collect spinal cord samples, it is not known if the signs would have progressed or if the disease would resolve had the horses remained alive. Horse four started showing slight clinical signs near the end of the study although organisms had been recovered at seven days from her CSF. Significant gross lesions were seen in the Pilot horse (EXAMPLE 4) while horse 3 and 4 had mild hemorrhage and petechial lesions in several sections of the spinal cord.

This study successfully demonstrates a dose titration effect of *S. neurona* when following the methods of the disclosure herein.

The pathophysiology of natural *Sarcocystis neurona* infection in the horse is unknown. Equine infections by *S. neurona* may involve a hematogenous phase, although previous introduction of culture derived merozoites in the peripheral blood or directly in the CNS have been unsuccessful.[15] *Sarcocystis neurona* can enter a variety of host cells but vary in their response to calcium ionophore (A23187).[16] When parasites were released from host cells by A23187 the conoid was extruded. The position of the conoid in intracellular versus extracellular parasites was also shown in ultrastructure studies by Speer and Dubey (FIGS. 5 and 6). *Sarcocystis neurona* is an obligate intracellular pathogen, probably utilizing the conoid and associated proteins for host cell invasion. Extracellular parasites, that have extruded the conoid without attaching to a host cell, are rendered impotent, unable to infect new host cells. It is not known what stimulus causes the release of *S. neurona* from host cells; release may be dependent on the host cell type, ion exchange across cell membranes, or the stimulus could be cell death. It is important to maintain the parasite in an environment protects parasite infectivity when trying to reproduce disease in the horse.

As a result of the studies described in EXAMPLES 4 and 5, the inventors concluded that the pathophysiology of *S. neurona* infection in horses includes a parasitemia. The parasite resides inside host lymphocyte cells thereby evading the hosts immune system so as to obtain entry into the CNS. In this model of *S. neurona* infection in the horse a relationship is shown between clinical EPM in the horse and the number of parasites successfully entering peripheral host cells with subsequent transport to the central nervous system. The dose of *S. neurona* merozoites required to produce clinical signs, spinal cord lesions, and recovery of the parasite from the CNS was examined using a time frame that recognizes the constraints of drug and vaccine testing. In addition to drug and vaccine testing the model of *S. neurona* encephalitis disclosed in this invention can help answer important questions such as the recrudescence of disease in infected animals and the part *S. neurona* plays in lameness in the poorly performing horse.

EXAMPLE 6

Development of a Diagnostic Test Using the Equine Model of EPM Using RT-PCR for the Detection of IFN γ Production in Response to rSnSAG1 Antigen The most commonly accepted methods of diagnosis of *S. neurona* infection are clinical signs in conduction with antibodies in the serum and cerebrospinal fluid. Necropsy with subsequent postmortem histologic examination of neurologic tissues or culture of the organism from the central nervous system of the horse are the most specific method of diagnosis of EPM, but used rarely. Serology and spinal fluid analysis demonstrating antibodies against *S. neurona* are used commonly to diagnosis infection. Although serology can be used to document exposure to parasites thought to cause EPM, horses apparently can be exposed frequently without ever developing clinical disease.[14] The most common clinical signs reportedly seen among horses with EPM are ataxia, limb weakness, and lameness. We have demonstrated that horses with *S. neurona* in the CNS with dramatic changes in the CSF did not evidence lameness until seven days later. The equine model of EPM described herein has correlated the degree of clinical signs seen in the infected horse with experimentally induced parasitemia and subsequent recovery of *S. neurona* from the CNS of horses irrespective of serological status.

In this study, the equine model of EPM disease described herein was used to determine whether the presence or absence of Interferon gamma (IFN γ) specific for SnSAG1 as assayed by RT PCR indicated EPM. The Pilot horse in EXAMPLE 4 and the four horses from EXAMPLE 5 were tested prior to infection, after infection and after development of clinical signs of EPM using the IFN γ specific for rSnSAG1 (the major surface antigen of *S. neurona*) as assayed by RT PCR. White blood cells from each animal were tested once a week for IFN γ stimulation by rSnSAG1. Serum samples from each horse were also obtained each week and were evaluated for IgG to rSnSAG1 by direct ELISA The procedure for the IFN γ assay was as follows. Recombinant protein (rSnSAG1) was prepared from *E. coli* or yeast by art known techniques, diluted, and added to each well of a 96 well plate to yield 2 μg recombinant protein per well. The plate was incubated overnight at 4° C. and then washed in sterile phosphate buffered saline (PBS). Fresh lymphocytes from each horse were collected as described previously. Lymphocytes were added to a 96 well culture plate that had been coated with 1 μg rSnSAG1 and incubated for 24, 48, 72, and 96 hours. At each time point the stimulated lymphocytes were removed to a microfuge tube containing 50 μl RNAlater (Ambion). RNA was isolated using 200 μl Trizol reagent and using a phenol-chloroform extraction procedure. Following a second extraction with phenol, chloroform, and isoamyl alcohol, the RNA was precipitated using 20 μl ammonium acetate (3M, pH 4.2) and 250 μl isopropyl alcohol and incubated at −20° C. for one hour or overnight. The RNA was pelleted by centrifugation for 30 min in a microfuge and the pellet washed in 95% EtOH. The pellet was resuspended in 50 μl nuclease free water. A reaction mixture of 5 μl RNA, 3 μl 12 mM dNTP's, 1 μl oligo dT primer, and 7 μl water was heated to 80° C. for three minutes and cooled on ice. Each tube received 4 μl 5×buffer, 1 μl reverse transcriptase, and 1 μl RNase inhibitor. The reaction was incubated at 42° C. for 1 hour. The cDNA was cooled on ice and 5 μl aliquot added to a PCR reaction containing 3 μl 12 mM dNTP's, 5 μl 10×buffer, and 1 μl each forward and reverse equine IFN γ primer (5'aacctgaggaagcggaagaggagt3' forward, 3' ttggactccttcgccttctcct5' reverse), 1 U TAQ polymerase, and 35 μl water. The amplification conditions were 94° C. for 4 min followed by 35 cycles: 94° C. 45 sec, 60° C. 45 sec, and 72° C. 2 min. The 487 bp amplicon representing the equine IFN γ mRNA sequence was visualized by electrophoresis using 2% agarose. A sample was determined as positive if the 487 bp amplicon was present and a sample was determined negative if there was no amplification using the IFN primers. The results for horses with EPM have consistently been negative while horses that are not infected with S. neurona or have been successfully treated for S. neurona EPM are positive for the amplicon in this test. The results of testing the high dose horse, medium dose horse and low dose horse as well as the control horse (from EXAMPLE 6) are shown in the graph in FIG. 7. It is clear that all horses were able to stimulate interferon γ production prior to being infected and all but the control horse lost the ability to stimulate interferon γ to rSnSAG1 after infection. It is also important to note that the loss of the interferon γ response to rSnSAG1 was dose related over time. The high and mid-dose horses lost the ability to respond sooner than the low-dose horse.

EXAMPLE 7

Infection of an Intermediate Host to Demonstrate a Mouse Model of EPM Infection in a Fetus Mouse hybridoma cells (S20) were infected with S. neurona as described in EXAMPLE 1. After 24 hours incubation $10^5$ infected cells were separated by density gradient separation to remove uninfected cells. Infected cells were injected intraperitoneally into 4 mice and the mice were bred the same day. Additionally, four mice were not infected with S. neurona and bred on the same day. Two of the uninfected, pregnant mice were then challenged at day 12 with mouse hybridoma cells that had been infected with S. neurona as previously described. Two mice served as uninfected pregnant controls. At 18 days post breeding the mice (n=8) were sacrificed and tissues including lung, liver, spleen, brain, and uterus were placed in zinc buffered formalin. The fixed tissues were used to prepare thin sections on slides coated for immunohistochemistry. Control samples for immunohistochemistry included thin sections of brain tissues from SCID mice that were infected (positive control) and were not infected (negative control) with S. neurona by sporocyst infection that produced brain schizonts in the infected mice. The results of the mouse infection study showed that the adult mice (n=8) did not have S. neurona merozoites present in lung, liver, spleen or brain tissue sections when monoclonal antibodies (mAb) to the SAG1 protein of S. neurona was used in IHC studies. The mice (n=2) that were infected after day 12 of gestation had normal pups in the uterus and these tissues did not stain with mAb to the SAG1 protein of S. neurona. However, the mice (n=4) that were bred on the challenge day had no viable pups in the uterine tissues and had merozoites present in these tissues as demonstrated by binding of mAb to SAG1 protein by IHC. The unchallenged mice (n=2) had viable pups in the uterus that did not have demonstrable organisms by IHC.

This study demonstrated that when a mouse is infected with S. neurona according to this invention, and then bred prior to 12 days of gestation, S. neurona will infect lymphocyte cells in the experimental animals and invade and replicate in fetal tissues. This is the first demonstration of the successful experimental infection of an immunocompetent mouse with S. neurona and the first transmission of S. neurona across the placental barrier to produce infection in fetal tissues (vertical transmission).

EXAMPLE 8

Infection of an Intermediate Host to Demonstrate an Equine Model of EPM Infection in a Fetus In a second example of vertical transmission, and a confirmation of the mouse study, a pregnant mare was infected as previously described in EXAMPLE 4. This mare became infected with S. neurona as demonstrated by isolation of the organism from the CNS of the mare at day 7 and 64 and cultivating the isolated S. neurona in vitro. The mare developed mild signs of weakness, mild one-sided facial paresis, and lameness recognized at a trot. After 64 days infection, the pregnant mare was euthanized and tissue samples were removed from the fetus. S. neurona was demonstrated in the fetal lung tissues on thin sections by both IHC and Wright-Geims stained sections.

This study demonstrated that the equine model of EPM infection described herein produced vertical transmission to an equine fetus. This is the first demonstration of the successful experimental infection of an immunocompetent equine with S. neurona to produce infection in the fetal tissues. It is suggested that this infection must be established prior to the production of interferon gamma by the fetus.

It will be appreciated that the instant specification and claims are set forth by way of illustration and not limitation, and that various modifications and changes may be made without departing from the spirit and scope of the present invention.

What is claimed is:

1. A method for reproducing an Apicomplexan parasite disease in a non-human mammalian host, said method comprising:
   infecting an isolated susceptible cell homologous to the mammalian host with a merozoite stage of the Apicomplexan parasite;
   inoculating said infected susceptible homologous cell into said host; and
   monitoring said host for signs of the Apicomplexan parasite disease.

2. The method of claim 1 wherein the Apicomplexan parasite is selected from Sarcocystis dasypus (syn. S.

*neurona*), *Sarcocystis neurona, Sarcocystis falcatula, Toxoplasma gondil, Neospora caninum, Neospora hughesi, Samocystis cruzi,* Sarcocystis spp., Eimeria spp. and Plasmodium spp.

3. The method of claim 1 wherein the mammalian host is selected from the group consisting of equines, bovines, canines, felines, goats, sheep, mice, rats, guinea pigs, rabbits, and hamsters.

4. The method of claim 1 wherein the susceptible homologous cell is selected from human, equine, bovine, canine, feline, porcine, caprine, ovine and murine cells.

5. The method of claim 1 wherein infecting is by a route selected from intravenous, intramuscular, subcutaneous, intranasal, intraperitoneal, intratracheal, intrathecal and combinations thereof.

6. The method of claim 1, wherein the infected susceptible homologous cell consists of a leukocyte comprising at least a merozoite stage of a parasite selected from *Sarcocystis neurona, Sarcocystis falcatula,* and *Neurosporosis hughesi,* said merozoite having an unextruded conoid.

7. The method of claim 6, wherein the leukocyte consists of an equine leukocyte.

8. The method of claim 6, wherein the leukocyte is selected from a lymphoid leukocyte, a myeloid leukocyte, and mixtures thereof.

9. The method of claim 6, wherein the leukocyte comprises a lymphoma cell.

10. The method of claim 6, wherein the leukocyte comprises an activated leukocyte.

11. The method of claim 6, wherein the infected leukocyte is made by a process comprising:

obtaining blood from a mammalian host;

isolating the leukocyte from the obtained blood;

infecting the isolated leukocyte with a competent stage of the selected parasite; and monitoring the infected leukocyte until a parasite merozoite having an unextruded conoid is present therein.

12. The method of claim 11, further comprising culturing the isolated leukocyte.

* * * * *